United States Patent [19]
Belfield et al.

[11] Patent Number: 5,972,962
[45] Date of Patent: Oct. 26, 1999

[54] TREATMENT OF PRURITUS

[75] Inventors: Eric George Belfield; Ivan Tommasini, both of Sandwich, United Kingdom

[73] Assignee: Pfizer Inc., New York, N.Y.

[21] Appl. No.: 09/196,054

[22] Filed: Nov. 20, 1998

[30] Foreign Application Priority Data

Nov. 28, 1997 [GB] United Kingdom ................... 9725114

[51] Int. Cl.⁶ .................................................. A61K 31/445
[52] U.S. Cl. .......................... 514/315; 514/316; 514/318; 514/320; 514/331
[58] Field of Search .................................... 514/315, 316, 514/318, 320, 331

[56] References Cited

U.S. PATENT DOCUMENTS

| | | | |
|---|---|---|---|
| 4,181,726 | 1/1980 | Bernstein | 424/260 |
| 5,064,834 | 11/1991 | Zimmerman et al. | 514/279 |
| 5,159,081 | 10/1992 | Cantrell et al. | 546/226 |
| 5,250,542 | 10/1993 | Cantrell et al. | 514/315 |

FOREIGN PATENT DOCUMENTS

| | | |
|---|---|---|
| 0278339 | 10/1988 | European Pat. Off. . |
| 0506468 | 9/1992 | European Pat. Off. . |
| 0506478 | 9/1992 | European Pat. Off. . |
| 1525584 | 9/1978 | United Kingdom . |
| WO8400899 | 3/1984 | WIPO . |

OTHER PUBLICATIONS

D.M. Zimmerman et al., in "Structure —Activity Relationships of trans–3,4–Dimethyl–4–(3–hydroxyphenyl)piperidine Antagonists for μ and κ–Opioid Receptors," *Journal of Medicinal Chemistry*, vol. 36, p. 2833 (1993).

Charles H. Mitch et al., in 3,4–Dimethyl–4–(3–hydroxyphenyl)piperidines: Opioid Antagonists with Potent Anorectant Activity, *Journal of Medicinal Chemistry*, vol. 36, p. 2842 (1993).

*Primary Examiner*—Raymond Henley, III
*Attorney, Agent, or Firm*—Peter C. Richardson; Paul H. Ginsburg

[57] ABSTRACT

The use of certain known 1,3,4 trisubstituted 4-aryl-piperidines for the treatment of pruritus in humans and animals is disclosed.

6 Claims, No Drawings

TREATMENT OF PRURITUS

BACKGROUND OF THE INVENTION

This invention relates to the use of certain 4-phenylpiperidines in the treatment of pruritus, including allergic dermatitis and atopy, in animals and humans.

Itching or pruritus is a common dermatological symptom which can give rise to considerable distress, in both humans and animals. Pruritus is often associated with inflammatory skin disease which can commonly be caused by hypersensitivity reactions (such as reaction to insect bites e.g. flea bites, or to environmental allergens such as house dust mite or pollen), bacterial and fungal infections of the skin or ectoparasite infections. Previous treatments for pruritus include the use of corticosteroids and antihistamines, however both have undesired side effects. Other therapies include the use of essential fatty acid dietary supplements which are slow to act and offer only limited efficacy against allergic dermatitis.

WO84/00889 and U.S. Pat. No. 4,181,726 disclose the use of the opioid antagonist naloxone in the treatment of pruritus, however naloxone has not been commercially exploited for the control of pruritus, and there is a continuing need for a cheap and effective remedy.

Certain 1,3,4-trisubstituted 4-aryl-piperidine derivatives are disclosed in GB-A-1525584 as potent narcotic antagonists which also display analgesic properties. These compounds are also claimed in EP-A-0287339 as opioid antagonists which block the effect of agonists at the mu or kappa receptors, having potential utility in treating a variety of disorders associated with these receptors such as eating disorders, opiate overdose, depression, smoking, alcoholism, sexual dysfunction, shock, stroke, spinal damage and head trauma. The structure activity relationships of this series of compounds is reviewed in J. Medicinal Chemistry, 1993, 36, 2833 and their effect on food consumption in obese Zuker rats is described in J. Medicinal Chemistry 1993, 36, 2842. Potential utility is suggested as an appetite suppressant for weight loss. Further related 1-N-substituted-4-aryl piperidines are disclosed as peripherally selective opioid antagonists in EP-A-0506468 and EP-A-0506478. Potential utility is suggested in preventing peripherally mediated undesired opiate effects and in relieving the symptoms of idiopathic constipation and irritable bowel syndrome. We have now unexpectedly discovered that such compounds also have activity as antipruritic agents.

SUMMARY OF THE INVENTION

Thus the present invention provides for the use of a compound for the preparation of a medicament for use in the treatment of pruritus in a human or animal, wherein said compound is:

(i) a compound of formula 1:

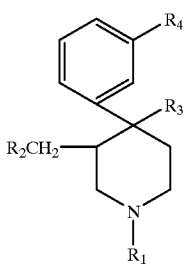

Formula I wherein in formula I above $R_1$ is $C_1$–$C_8$ alkyl, $C_3$–$C_8$ alkenyl, $C_3$–$C_8$ alkynyl, $C_4$–$C_8$ (cycloalkyl)alkyl,

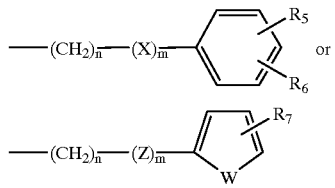

wherein:

n is 1, 2 or 3;

m is 0 or 1;

X is C(=O), CH(OH), CH=CH, S, O, or $NR_8$, wherein:

$R_8$ is H, $C_1$–$C_4$ alkyl or $C_1$–$C_4$ alkanoyl;

Z is C(=O), CH(OH), or CH=CH;

W is O or S;

$R_5$ is $C_1$–$C_3$ alkylthio, nitro, amino, trifluoromethyl, hydroxy, or $R_6$;

$R_6$ is H, $C_1$–$C_3$ alkyl, $C_1$–$C_3$ alkoxy, or halogen;

$R_7$ is H or methyl;

$R_2$ is H, $C_1$–$C_4$ alkyl, or $C_2$–$C_6$ alkenyl;

$R_3$ is $C_1$–$C_4$ alkyl or $C_2$–$C_6$ alkenyl; and $R_4$ is H, hydroxy, $C_1$–$C_3$ alkoxy, $C_1$–$C_{12}$ alkanoyloxy, or

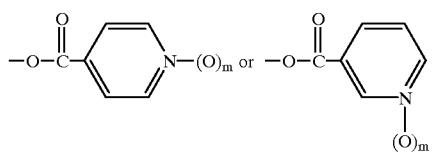

or a pharmaceutically or veterinarily acceptable salt thereof; with the limitation that when X or Z is CH(OH) or C(=O), n is other than 3; or (ii) a compound of the formula 2:

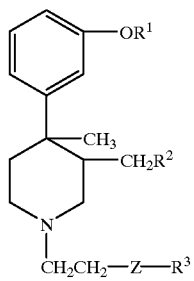

Formula 2 wherein in formula 2 above $R^1$ is H or $C_1$–$C_4$ alkanoyl;

$R^2$ is H, $C_1$–$C_4$ alkyl or $C_2$–$C_6$ alkenyl;

$R^3$ is $C_4$–$C_8$ cycloalkyl, $C_4$–$C_8$ cycloalkenyl, $C_1$–$C_6$ alkyl, $C_2$–$C_6$ alkenyl, $C_1$–$C_4$ alkyl substituted $C_4$–$C_8$ cycloalkyl, $C_1$–$C_4$ alkyl substituted $C_4$–$C_8$ cycloalkenyl or thienyl;

Z is CH($OR^4$), (C=O) or a bond;

$R^4$ is hydrogen, $C_1$–$C_6$ alkyl,

$R^5$ is $C_1$–$C_4$ alkyl or

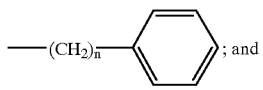
; and n is 1, 2 or 3;

or a pharmaceutically or veterinarily acceptable salt thereof; or (iii) A compound of formula 3:

Formula 3

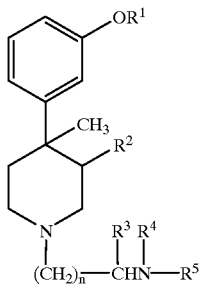

wherein in formula 3 above $R^1$ is H or $(C_1$–$C_5)$ alkyl;

$R^2$ is H, $(C_1$–$C_5)$ alkyl, or $(C_2$–$C_6)$ alkenyl;

$R^3$ is H, $(C_1$–$C_{10})$ alkyl, $(C_3$–$C_8)$ cycloalkyl; $(C_3$–$C_{10})$ alkenyl, $(C_3$–$C_8)$ cycloalkyl-$(C_1$–$C_3)$ alkyl, phenyl, $(C_5$–$C_8)$ cycloalkenyl, $(C_5$–$C_8)$ cycloalkenyl-$(C_1$–$C_3)$ alkyl, or phenyl-$(C_1$–$C_3)$alkyl;

$R^4$ is H, $(C_3$–$C_8)$ cycloalkyl, $(C_1$–$C_{10})$ alkyl, $(C_3$–$C_{10})$ alkenyl, $(C_3$–$C_8)$ cycloalkyl-$(C_1$–$C_3)$alkyl, phenyl or phenyl-$(C_1$–$C_3)$ alkyl;

$R^5$ is H, $(C_1$–$C_{10})$alkyl $(C_1$–$C_{10})$alkanoyl, $C(O)CH$—$[(CH_2)_3NHC(NH)NHNO_2]$—$NHC(O)W$, $C(O)NH(C_1$–$C_{10})$alkyl, $[C(O)$—$(CH_2)_mC(O)]_qR^6$, or $[C(O)(CH_2)_mNHC(O)]_q$–$R^{6-}$, W is $(C_1$–$C_{10})$alkyl, $O(C_1$–$C_{10})$alkyl, $(C_1$–$C_4$alkyl)-NHC$(O)(C_1$–$C_6)$-alkyl, or $(C_1$–$C_4$ alkyl)$C(O)NHB$, where B is $(C_1$–$C_{10})$-alkyl, phenyl or phenyl-$(C_1$–$C_3)$ alkyl;

$R^6$ is $OR^7$; $NHR^7$, $OCH_2C(O)NR^8R^9$, $O(C_1$–$C_4)$alkyl)OC—$(O)R^{10}$, $(C_1$–$C_{10})$alkyl or $NHCHR^{11}C(O)R^{12}$ –, $R^7$ is H, $(C_1$–$C_{10})$alkyl, $(C_3$–$C_8)$cycloalkyl, $(C_3$–$C_8)$ cycloalkyl-$C_1$–$C_3)$alkyl or $(CH_2)_mC(O)NR^8R^{9-}$, $R_8$ is H, or $(C_1$–$C_{10})$alkyl;

$R^9$ is H, or $(C_1$–$C_{10})$alkyl;

$R^{10}$ is $(C_1$–$C_{10})$ alkyl, $(C_3$–$C_8)$ cycloalkyl, or

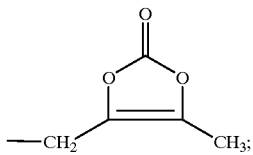

$R^{11}$ is H, $(C_1$–$C_{10})$alkyl, or phenyl-$(C_1$–$C_3)$alkyl;

$R^{12}$ is $OR^{13}$ or $NR^{13}R^{14}$;

$R^{13}$ is H or $(C_1$–$C_{10})$alkyl;

$R^{14}$ is H or $(C_1$–$C_{10})$alkyl;

n=1–3;

m=1–3;

q=1–3; or a pharmaceutically or veterinarily acceptable salt thereof; or (iv) A compound of formula 4

Formula 4

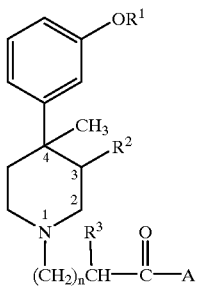

wherein in formula 4 above;

$R_1$ is H or $C_1$–$C_5$ alkyl;

$R_2$ is H, $C_1$–$C_5$ alkyl or $C_2$–$C_6$ alkenyl;

$R_3$ is H, $C_1$–$C_{10}$ alkyl, $C_1$–$C_{10}$ alkenyl, phenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;

A is $OR^4$ or $NR^5R^6$;

wherein:

$R^4$ is H, $C_1$–$C_{10}$ alkyl $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;

$R^5$ is H or $C_1$–$C_3$ alkyl;

$R^6$ is H, $C_1$–$C_{10}$ alkyl, $C_3$–$C_{10}$ alkenyl, cycloalkyl, phenyl, cycloalkyl-substituted $C_1$–$C_3$ alkyl, $C_5$–$C_8$ cycloalkenyl, $C_5$–$C_8$ cycloalkenyl-substituted $C_1$–$C_3$ alkyl, phenyl-substituted $C_1$–$C_3$ alkyl, or $(CH_2)_q$—B; or $R^5$ and $R^6$ are each $CH_2$ which together with N form a 4- to 6-membered heterocyclic ring;

wherein:

B is

or $NR^7R^8$ wherein:

$R^7$ is H or $C_1$–$C_3$ alkyl;

$R^8$ is H, $C_1$–$C_{10}$ alkyl, $C_3$–$C_{10}$ alkenyl, cycloalkyl-substituted $C_1$–$C_3$ alkyl, cycloalkyl, $C_5$–$C_8$ cycloalkenyl, $C_5$–$C_8$ cycloalkenyl-substituted $C_1$–$C_3$ alkyl, phenyl or phenyl-substituted $C_1$–$C_3$ alkyl; or $R^7$ and $R^8$ are each $CH_2$ which together with N form a 4- to 6-membered heterocyclic ring;

W is $OR^9$, $NR^{10}R^{11}$, or OE;

wherein:

$R^9$ is hydrogen, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;

$R^{10}$ is hydrogen or $C_1$–$C_3$ alkyl;

$R^{11}$ is hydrogen, $C_1$–$C_{10}$ alkyl, $C_3$–$C_{10}$ alkenyl, phenyl, cycloalkyl, $C_5$–$C_8$ cycloalkenyl, cycloalkyl-substituted $C_1$–$C_3$ alkyl, phenyl-substituted $C_1$–$C_3$ alkyl, or $$(CH_2)_m \overset{O}{\overset{\|}{C}} Y;$$

or $R^{10}$ and $R^{11}$ are each $CH_2$ which together with N form a 4- to 6-membered heterocyclic ring;

E is $$(CH_2)_m\overset{O}{\overset{\|}{C}}-D, \quad \begin{array}{c}H_3C\\-CH_2\end{array}\!\!\!\!\!\!\!\!=\!\!\!=\!\!\!O \quad \text{or} \quad -R^{12}-O\overset{O}{\overset{\|}{C}}R^{13}$$

wherein:

$R^{12}$ is $C_1$–$C_3$ alkyl substituted methylene, $R^{13}$ is $C_1$–$C_{10}$ alkyl;

D is $OR^{14}$ or $NR^{15}R^{16-}$;

wherein:

$R^{14}$ is H, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, or $C_5$–$C_8$ cycloalkenyl-substituted $C_1$–$C_3$ alkyl or phenyl-substituted $C_1$–$C_3$ alkyl;

$R^{15}$ is H, $C_1$–$C_{10}$ alkyl, $C_3$–$C_{10}$ alkenyl, phenyl, phenyl-substituted $C_1$–$C_3$ alkyl, cycloalkyl, $C_5$–$C_8$ cycloalkenyl, cycloalkyl-substituted $C_1$–$C_3$ alkyl or $C_5$–$C_8$ cycloalkenyl-substituted $C_1$–$C_3$ alkyl;

$R^{16}$ is H or $C_1$–$C_3$ alkyl;

$R^{15}$ and $R^{16}$ are each $CH_2$ which together with N form a 4- to 6-membered heterocyclic ring;

Y is $OR^{17}$ or $NR^{18}R^{19}$;

wherein:

$R^{17}$ is H, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl, or phenyl-substituted $C_1$–$C_3$ alkyl;

$R^{18}$ is hydrogen or $C_1$–$C_3$ alkyl;

$R^{19}$ is hydrogen, $C_1$–$C_{10}$ alkyl, $C_3$–$C_{10}$ alkenyl, phenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl, or phenyl-substituted $C_1$–$C_3$ alkyl; or $R^{18}$ and $R^{19}$ are each $CH_2$ which together with N form a 4- to 6-membered heterocyclic ring;

n is 0–4;

q is 1–4;

m is 1–4;

or a pharmaceutically or veterinarily acceptable salt thereof.

A particularly preferred group of compounds for use in the present invention are compounds of the formula 5:

Formula 5

(I)

and pharmaceutically or veterinarily acceptable salts thereof wherein in Formula 5 above:

$R^{20}$ is H or $C_1$–$C_4$ alkanoyl;

$R^{21}$ is $C_1$–$C_8$ alkyl, $C_3$–$C_8$ alkenyl, $C_3$–$C_8$ alkynyl, $C_3$–$C_8$ cycloalkyl($C_1$–$C_6$)alkyl, $C_5$–$C_8$ cycloalkenyl($C_1$–$C_6$) cycloalkyl, or a group of the formula —$(CH_2)_n$—G—$A^1$;

wherein n is 1, 2 or 3;

G is C=O, CH(OH), O, or a direct bond; and $A^1$ is $C_3$–$C_8$ cycloalkyl, phenyl, which may optionally be substituted with one or more substituents independently selected from halo, $C_1$–$C_4$ alkyl and $C_1$–$C_4$ alkoxy, or $A^1$ is thienyl, furyl, or pyridyl.

The invention also provides for a method of treating pruritus, in a human or animal which comprises administering a therapeutically or prophylactically effective amount of a compound of the formula 1, 2, 3, 4 or 5 as defined above, or a pharmaceutically or veterinarily acceptable salt thereof.

The piperidines of this invention form pharmaceutically or veterinarily acceptable acid addition salts with a wide variety of inorganic and organic acids. The particular acid used in salt formation is not critical; however, the corresponding salt that is formed must be substantially non-toxic to animals. Typical acids generally used include sulphuric, hydrochloric, hydrobromic, phosphoric, hydroiodic, sulfamic, citric, acetic, maleic, malic, succinic, tartaric, cinamic, benzoic, ascorbic and related acids. The piperidines additionally form quaternary ammonium salts, for example, with a variety of organic esters of sulphuric, hydrohalic and aromatic sulphonic acids.

The compounds of the invention contain one or more asymmetric centres and thus they can exist as enantiomers and diastereomers. The invention includes the use of both the separated individual isomers as well as mixtures of isomers.

DETAILED DESCRIPTION OF THE INVENTION

The compounds defined above for use in the present invention may be prepared according to the methods described in the publications mentioned above. Particularly preferred compounds for use in the treatment of pruritus include compounds of the formula (5) above wherein $R^{20}$ is H or $COCH_3$ and wherein $R^{21}$ is $C_2$ to $C_8$ alkyl, particularly n-hexyl or 2-methyl-pentyl, or $C_1$–$C_6$ alkyl substituted by $C_3$–$C_8$ cycloalkyl, particularly cyclohexylethyl.

While it is possible to administer a compound of the invention directly without any formulation, the compounds are preferably employed in the form of a pharmaceutical or veterinary formulation comprising a pharmaceutically or veterinarily acceptable carrier, diluent or excipient and a compound of the invention. Such compositions will contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristrate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.1 to 10% by weight of the active ingredient.

These formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

For veterinary use, the compounds of the invention are of particular value for treating pruritus in domestic animals such as cats and dogs and in horses. Thus the invention also provides a veterinary formulation comprising a compound of the formula 1, 2, 3, 4 or 5, as defined above, together with a veterinarily acceptable diluent or carrier. Such formulations include in particular ointments, pour-on formulations, spot-on formulations, dips, sprays, mousse, shampoo, collar and powder formulations.

As an alternative for treating animals, the compounds may be administered with the animal feedstuff and for this purpose a concentrated feed additive or premix may be prepared for mixing with the normal animal feed.

For human use the compounds are administered as a pharmaceutical formulation containing the active ingredient together with a pharmaceutically acceptable diluent or carrier.

The compounds of the invention are prepared using the procedures described in GB-A-1525584, EP-A-0287339, EP-A-0506468, EP-A-0506478 or in J. Medicinal Chemistry 1993, 36, 2833. The following examples are illustrative of the preparation of typical examples:

Melting points were determined using a Gallenkamp melting point apparatus and are uncorrected.

Nuclear magnetic resonance (NMR) spectral data were obtained using a Bruker AC300 or AM300 spectrometer, the observed chemical shifts ($\delta$) being consistent with the proposed structures.

Mass spectral (MS) data were obtained on a Finnigan Mat. TSQ 7000 or a Fisons Instruments Trio 1000 spectrometer. The calculated and observed ions quoted refer to the isotopic composition of lowest mass.

HPLC means high performance liquid chromatography.

Room temperature means 20 to 25° C.

EXAMPLES

Example 1

(±)-N-(n-Hexyl)-4-(3-hydroxyphenyl)-trans-3,4-dimethylpiperidine hydrochloride (i) To a stirred solution of 3-bromoanisole (12.83 g, 0.069 mol) in dry tetrahydrofuran (70 ml) at −50° C. under an atmosphere of nitrogen was added sec-butyllithium (1.3M in hexanes, 68.5 ml, 0.089 mol) dropwise, ensuring that the temperature in the reaction vessel did not rise above −50° C. After complete addition of the sec-butyllithium, a white precipitate formed, and the reaction was stirred for 1 hour at −50° C. N-Ethyl-4-(3-methoxyphenyl)piperidine (10.5 ml, 0.079 mol) in dry tetrahydrofuran (50 ml) was added dropwise at a rate to maintain the reaction temperature below −40° C., resulting in an orange solution. The reaction mixture was allowed to warm to −20° C. over 1.5 hours, and then to room temperature over a further 1 hour. After this time, the reaction mixture was quenched by the addition of saturated brine (21 ml) and water (30 ml). The quenched reaction was stirred for a further 30 minutes, and then the two phases separated, and the organic phase retained. The aqueous phase was extracted with dichloromethane (3×75 ml), and the two organics combined and washed with hydrochloric acid (1N, 2×50 ml). The aqueous layer was separated, basified with ammonium hydroxide to pH 10, and extracted with dichloromethane (3×40 ml). The dichloromethane extracts were concentrated to yield a thick oil, which was triturated in cold hexane until a solid was obtained. This crude solid was stirred in hot hexane, allowed to cool, and filtered to yield N-ethyl-4-hydroxy-4-(3-methoxyphenyl)piperidine (5.5 g, 33.7%) as a white solid. m.p.=86.7–91.1° C.

MS (thermospray): M/Z [MH$^+$]236.4; $C_{14}H_{20}NO_2$+H requires 236.2

(ii) p-Toluenesulphonic acid (0.56 g, 2.98 mmol) was added to a suspension of the above product (0.5 g, 1.49 mmol) in toluene, and heated under reflux for 2.5 hours employing a Dean and Stark apparatus. After this time, the reaction mixture was allowed to cool to room temperature, then water (4 ml) was added, and the resultant biphasic system was stirred vigorously for several minutes. The two phases were separated, and the toluene layer washed with water (2×3 ml). The aqueous portions were combined, made basic by addition of sodium hydroxide (1M, 0.2 ml) whereupon a white precipitate formed. The aqueous suspension was extracted with hexane (3×5 ml), dried ($Na_2SO_4$) and concentrated to produce 1,2,3,6-tetrahydro-4-(3-methoxyphenyl)-N-ethylpyridine as an oil (0.31 g), which was used without further purification.

MS (thermospray): M/Z [MH$^+$]218.3; $C_{14}H_{19}NO+H$ requires 218.2.

(iii) The above product was converted to (±)-N-ethyl-4-(3-methoxyphenyl)-trans-3,4-dimethylpiperidine hydrochloride following the procedures described by Zimmerman et al., J. Org. Chem., 1991, 56, 1660 for the corresponding N-methyl compound except that the hydrochloride salt was used in the recrystallisation step with 2-propanol. The product was obtained as a white crystalline solid which was used immediately in the next stage.

NMR(CDCl$_3$) (Selected data for free base): 0.8 (d, 3H), 1.05 (t, 3H), 1.3 (s, 3H), 1.6–1.8 (m, 2H), 3.8 (s, 3H), 2.3–2.65 (m, 6H), 6.7–7.3 (m, 4H).

MS (thermospray): M/Z [MH$^+$]248.3; $C_{16}H_{25}NO+H$ requires 248.3.

(iv) The free base of (±)-N-Ethyl-4-(3-methoxyphenyl)-trans-3,4-dimethylpiperidine was prepared by addition of 5N NaOH to an aqueous solution until the pH reached 9–10 (test paper). The resultant basic suspension was extracted into dichloromethane, the organic fractions were dried ($Na_2SO_4$) and concentrated to a thick oil in vacuo. The resultant free base (3.93 g, 0.016 mol) was combined with α-chloroethylchloroformate (3.35 ml, 0.032 mol) and heated under reflux for 5 hours. After this time, the excess reagent was removed in vacuo to produce a dark oil, which was taken up in methanol (15 ml) and heated under reflux for 1 hour. After this time, the methanol was removed in vacuo, and the resultant (±)-4-(3-methoxyphenyl)-trans-3,4-dimethylpiperidine (3.5 g), as a dark oil, was used without further purification.

NMR (CDCl$_3$) (Free base): 0.95 (d, 3H), 1.4 (s, 3H), 1.85 (m, 2H), 2.2 (bs, 1H), 2.5 (t, 1H), 3.2 (bt, 2H), 3.4 (m, 2H), 3.8 (s, 3H), 6.7–7.3 (m, 4H).

MS (thermospray): M/Z [MH$^+$]219.9; $C_{14}H_{21}NO+H$ requires 220.2.

(v) The above product was heated under reflux in HBr/glacial acetic acid following the procedure described by Zimmerman et al., J. Org. Chem., 1991, 56, 1660, to yield (±)-4-(3-hydroxyphenyl)-trans-3,4-dimethylpiperidine, as a pale brown solid (4.09 g). m.p. 179–180° C.

NMR (CDCl$_3$) (Selected data for free base): 0.75 (d, 3H), 1.40 (s, 3H), 6.7–7.2 (m, 4H).

MS (thermospray): M/Z [MH$^+$]206.5; $C_{13}H_{19}NO+H$ requires 206.2.

(vi) To a solution of (±)-4-(3-hydroxyphenyl)-trans-3,4-dimethylpiperidine (3 g, 15 mmol) in tetrahydrofuran (115 ml) was added (in order) acetic acid (0.84 ml, 15 mmol), hexanal (1.93 ml, 16 mmol) and finally sodium triacetoxyborohydride (4.92 g, 22 mmol) in ten equal portions over 5 minutes. The resultant mixture was stirred for 5.5 hours, filtered to remove a precipitate, and the collected solid washed with ethyl acetate. The combined organic fractions were washed with water (100 ml), saturated aqueous sodium hydrogen carbonate solution (2×75 ml) and dried over sodium sulphate. Filtration and removal of solvent in vacuo produced a thick brown oil, which was purified by silica (150 g) column chromatography, eluting with ethylacetate-:hexane (1:1)+0.5% ammonia. Concentration of appropriate fractions produced a pale oil, which was dissolved in dry ether (60 ml). Addition of 2 mol equivalents of 1N ethereal hydrogen chloride solution provided a precipitate which was collected by filtration and dried in a vacuum oven to yield the (±)-N-(n-hexyl)-4-(3-hydroxyphenyl)-trans-3,4-dimethylpiperidine hydrochloride (2.2 g, 45%) as a white solid. m.p.140.3–143.7° C.

NMR (CDCl$_3$) (Selected data for the free base): 0.75 (d, 3H), 0.85 (t, 3H), 1.15–1.25 (m, 6H), 1.3 (s, 3H), 2.0 (m, 1H), 2.35 (m, 4H), 2.6 (m, 2H), 6.55–7.2 (m, 4H).

MS (thermospray): M/Z [MH$^+$]290.2; $C_{19}H_{31}NO+H$ requires 290.3.

Example 2

Resolution of the enantiomers of (±)-N-(n-Hexyl)-4-(3-hydroxyphenyl)-trans-3,4-dimethylpiperidine The enantiomers of (±)-N-(n-hexyl)-4-(3-hydroxyphenyl)-trans-3,4-dimethylpiperidine were separated by preparative HPLC on a Chiralpak™ AD column, 25 cm×2.0 cm; Flow 9 ml min$^{-1}$; employing U.V. detection at 220 nm; eluent hexane:propan-2-ol(91:9)+1% (w/v) diethylamine.

Enantiomeric purity was determined using a Chiralpak™ AD column 25 cm×0.46 cm; Flow 1 ml min$^{-1}$; employing UV detection at 254 nm; eluent hexane:propan-2-ol (90:10)+1% diethylamine (w/v).

Fraction 1 gave the (R,R)-(+)-enantiomer (Retention time 4.02 min, 94.9% enantiomeric excess), NMR (CDCl$_3$) (Selected data for the free base): 0.75 (d, 3H), 0.85 (t, 3H), 1.15–1.25 (m, 6H), 1.3 (s, 3H), 2.0 (m, 1H), 2.35 (m, 2H), 6.55–7.2 (m, 4H).

MS (CI): M/Z [MH$^+$]290.3; $C_{19}H_{31}NO+H$ requires 290.3.

Fraction 2 the (S,S)-(−)-enantiomer (Retention time 4.82 min, 91.2% enantiomeric excess), NMR (CDCl$_3$) (Selected data for the free base): 0.75 (d, 3H), 0.85 (t, 3H), 1.15–1.25 (m, 6H), 1.3 (s, 3H), 2.0 (m, 1H), 2.35 (m, 4H), 2.6 (m, 2H) 6.55–7.2 (m, 4H).

MS (CI): M/Z [MH$^+$]290.3; $C_{19}H_{31}NO+H$ requires 290.3.

Example 3

(±)-4-(3-Hydroxyphenyl)-trans-3,4-dimethyl-N-(4-methylpentyl)piperidine hydrochloride Experimental carried out by reaction of (±)-4-(3-hydroxyphenyl)-trans-3,4-dimethylpiperidine with 4-methylvaleric acid and oxalyl chloride in direct analogy with Zimmerman et al., J. Med. Chem., 1993, 36, 2842. The product was obtained as an oil which was converted to the hydrochloride salt as previously described in example 1(vi) and isolated as an off-white solid m.p. 176–178° C.

NMR (CDCl$_3$) (Selected data for the free base): 0.8 (d, 3H), 0.9 (d, 6H), 1.3 (s, 3H), 6.6–7.2 (m, 4H).

MS (thermospray): M/Z [MH$^+$]290.4; $C_{19}H_{31}NO+H$ requires 290.4.

Example 4

(±)-4-(3-Hydroxyphenyl)-trans-3,4-dimethyl-N-[3-(thien-3-yl)prop-1-yl]piperidine To a solution of (±)-4-(3-hydroxyphenyl)-trans-3,4-dimethylpiperidine (0.2 g, 0.97 mmol) in pyridine (5 ml)

was added a solution of thiophene-3-propionyl chloride (187 mg, 10.7 mmol) made from thiophene-3-propionic acid (prepared by the method of Mihailo, Mihailovic and Tot (J. Org. Chem, 1957, 22, 653)) and thionyl chloride in pyridine (5 ml). The resultant mixture was allowed to stir overnight at ambient temperature. The pyridine was removed on a rotary evaporator and the product dissolved in ethyl acetate (20 ml). This solution was washed with 20% w/v aqueous citric acid (5 ml), water (5 ml), brine (5 ml) and finally dried over sodium sulphate. The solvent was removed on a rotary evaporator to yield an amber gum (135 mg).

MS (thermospray): M/Z [MH$^+$]344.1; $C_{20}H_{25}NO_2S+H$ requires 344.1.

The gum was dissolved in tetrahydrofuran (5 ml). To this solution, purged with dry nitrogen and stirred at ambient temperature, was added a 1.0M solution (in diethyl ether) of lithium aluminium hydride (390 µl, 0.39 mmol) cautiously and stirring continued for 30 minutes. TLC of the reaction mixture (silica plate eluted with dichloromethane containing 10% v/v of methanol) indicated absence of starting material. The reaction mixture was quenched with ethyl acetate (10 ml) and after 5 minutes water (10 ml). After filtration to remove emulsifying solids the layers were separated and the aqueous re-extracted with ethyl acetate (10 ml). The combined extracts were washed with water (5 ml) then brine (5 ml) and the solvent removed on a rotary evaporator. The product was purified by column chromatography on silica eluting with dichloromethane containing 5% of methanol to give the title compound (22 mg, 7% over two steps).

NMR (CDCl$_3$) (Selected data for the free base): 0.8 (d, 3H), 1.3 (s, 3H), 1.65 (broad d, 1H), 1.9 (m, 2H), 2.05 (broad m, 1H), 2.9 (broad m, 1H), 6.6–7.3 (m, 7H).

MS (thermospray): M/Z [MH$^+$]330.4; $C_{20}H_{27}NOS+H$ requires 330.18.

Example 5

(±)-N-(2-Cyclohexylethyl)-4-(3-hydroxyphenyl)-trans-3,4-dimethylpiperidine hydrochloride Experimental carried out by reaction of (±)-4-(3-hydroxyphenyl)-trans-3,4-dimethylpiperidine with cyclohexane acetic acid and oxalyl chloride in direct analogy with Zimmerman et al., J. Med. Chem., 1993, 36, 2842. The product was obtained as an oil which was converted to the hydrochloride salt as previously described in example 1(vi) and isolated as a white solid m.p. 204–207° C.

NMR (CDCl$_3$) (Selected data for the free base) 0.8 (d, 3H), 0.9–2.8 (m, 13H), 2.0 (m, 1H), 2.3 (m, 2H), 2.5 (m, 2H), 2.8 (m, 2H), 6.6–7.2 (m, 4H).

MS (thermospray): M/Z [MH$^+$]316.4 $C_{21}H_{33}NO+H$ requires 316.4.

Example 6

(±)-4-(3-Hydroxyphenyl)-trans-3,4-dimethyl-N-[3-(thien-2-yl)prop-1-yl]piperidine 3-(2-Thiophene)propanoic acid (220 mg, 1.4 mmol) [prepared in direct analogy with Toth et al., Synth. Commun. 1995, 25, 3067], 1-hydroxybenzotriazole (204 mg, 1.5 mmol), 1-(3-dimethylaminopropyl)-3-ethylcarbodiimide hydrochloride (320 mg, 2.0 mmol) and dimethylformamide (50 ml) were stirred together at room temperature until all the solids had dissolved. (±)-4-(3-hydroxyphenyl)-trans-3,4-dimethylpiperidine (300 mg, 1.5 mmol) was added and the reaction mixture allowed to stir at room temperature for 18 hours. After this time the reaction mixture was diluted with water (25 ml) and extracted with diethyl ether (25 ml). The diethyl ether extract was dried (Na$_2$SO$_4$) and concentrated in vacuo to produce a clear colourless oil. The crude product was purified by silica (10 g) column chromatography, eluting with ethyl acetate. The appropriate fractions were combined and concentrated in vacuo to yield 300 mg of a white solid. This solid was then dissolved in anhydrous tetrahydrofuran (25 ml) and a 1M solution of lithiumaluminium hydride in diethyl ether (10 ml) was added to the solution. The reaction was stood at room temperature for 15 minutes then diluted with water (25 ml) and extracted with ethyl acetate (25 ml). The ethyl acetate extract was dried (Na$_2$SO$_4$) and concentrated in vacuo to produce the title compound as a clear brown oil (310 mg, 64% over two steps).

NMR (CDCl$_3$) (Selected data for the free base) 0.85 (d, 3H), 1.30 (s, 3H), 6.65 (d, 1H), 6.8 (s, 1H), 6.85 (d, 1H), 6.90 (dd, 1H), 7.10–7.20 (m, 3H).

MS (thermospray): M/Z [MH$^+$]330.4; $C_{20}H_{27}NOS+H$ requires 330.18.

Example 7

(±)-4-(3-Hydroxyphenyl)-trans-3,4-dimethyl-N-(3-phenylpropyl)piperidine

To a stirred solution of (±)-4-(3-hydroxyphenyl)-trans-3,4-dimethylpiperidine (0.15 g, 0.731 mmol) in dimethylformamide (5 ml) was added sodium hydrogen carbonate (0.068 g, 0.804 mmol) and 1-bromo-3-phenylpropane (0.16 g, 0.804 mmol). The stirred reaction mixture was heated under reflux for 1.5 hours, then quenched with water (20 ml) and extracted with diethyl ether (2×20 ml). The organic fractions were washed with saturated brine (20 ml), dried (Na$_2$SO$_4$), filtered and concentrated in vacuo to give the crude product which was purified by silica (15 g) column chromatography, eluting with dichloromethane, followed by dichloromethane:ethanol:0.880 ammonia (100:8:1), to give the title compound as a brown oil, (209 mg, 88%).

NMR (CDCl$_3$) (Free base): 0.8 (d, 3H), 1.3 (s, 3H), 1.6 (m, 1H), 1.7–1.9 (m, 2H), 1.9–2.1 (m, 2H), 2.2–2.5 (m, 4H), 2.5–2.7 (m, 4H), 2.9 (m, 1H), 6.5–6.6 (m, 1H), 6.7–6.8 (m, 2H), 7.1–7.3 (m, 6H).

MS (electrospray): M/Z [MH$^+$]324.2; $C_{22}H_{29}NO+H$ requires 324.23.

Example 8

(±)-4-(3-Hydroxyphenyl)-trans-3,4-dimethyl-N-(2-phenoxyethyl)piperidine

A dry round-bottomed flask, equipped with a reflux condenser and a nitrogen inlet, was charged with (±)-4-(3-hydroxyphenyl)-trans-3,4-dimethylpiperidine (82 mg, 0.4 mmol), 2-(phenoxy)ethylbromide (88 mg, 0.44 mmol), sodium hydrogen carbonate (37 mg, 0.44 mmol) and dimethylformamide (5 ml). The stirred reaction mixture was heated at 50° C. for 36 hours, then it was cooled to room temperature and diluted with dichloromethane (30 ml). The resultant solution was washed with saturated aqueous sodium hydrogen carbonate solution (30 ml), and the organic layer was retained. The aqueous layer was re-extracted with more dichloromethane (2×30 ml), and the organic fractions combined, washed with brine (25 ml), dried (Na$_2$SO$_4$), filtered and concentrated in vacuo to give a brown oil. This was purified by silica column chromatography (1:98.9:0.1 to 2:97.8:0.2 methanol:dichloromethane:-ammonia), to yield the title compound as a pale yellow oil, (33 mg, 25%).

NMR (C$_6$D$_6$) (Selected data for the free base): 0.9 (d, 3H), 1.15 (s, 3H), 3.9 (t, 2H), 6.6–7.1 (m, 9H).

MS (API+): M/Z [MH$^+$]326.2; C$_{21}$H$_{27}$NO$_2$+H requires 326.43.

Example 9

(±)-N-(3-Cyclohexylpropyl)-4-(3-hydroxyphenyl)-trans-3,4-dimethylpiperidine

A dry round-bottomed flask, equipped with a reflux condenser and a nitrogen inlet, was charged with (±)-4-(3-hydroxyphenyl)-trans-3,4-dimethylpiperidine (82 mg, 0.4 mmol), 3-(cyclohexyl)chloropropane (71 mg, 0.4 mmol), sodium hydrogen carbonate (37 mg, 0.44 mmol), sodium iodide (3 mg, 0.02 mmol) and dimethylformamide (5 ml). The stirred reaction mixture was heated at 70° C. for 8 hours, then it was cooled to room temperature and quenched with water (30 ml). The resultant mixture was extracted with dichloromethane (30 ml), and the organic layer retained. The aqueous was re-extracted with dichloromethane (2×20 ml), and the organic portions were combined, washed with brine (40 ml), dried (Na$_2$SO$_4$), filtered and concentrated in vacuo, to afford the crude material. This was purified by silica column chromatography, eluting with a gradient system of 1:98.9:0.1 to 2:97.8:0.2 methanol:dichloromethane:ammonia to give the title compound as a colourless viscous oil, (56 mg, 42%).

NMR (C$_6$D$_6$) (Selected data for the free base): 0.9 (d, 3H), 1.2 (s, 3H), 1.8 (m, 1H), 2.8 (m, 1H), 6.6–7.1 (m, 4H).

MS (API+): M/Z [MH$^+$]330.3; C$_{22}$H$_{35}$NO+H requires 330.49.

Example 10

(±)-4-(3-Hydroxyphenyl)-N-((R)-3-hydroxy-3-phenylpropyl)-trans-3,4-dimethylpiperidine A dry round-bottomed flask, equipped with a reflux condenser and a nitrogen inlet, was charged with (±)-4-(3-hydroxyphenyl)-trans-3,4-dimethylpiperidine (82 mg, 0.4 mmol), R-(+)-1-chloro-3-hydroxy-3-phenylpropane (75 mg, 0.44 mmol), sodium hydrogen carbonate (37 mg, 0.44 mmol), sodium iodide (6 mg, 0.04 mmol) and dimethylformamide (5 ml). The stirred reaction mixture was heated at 80° C. for 16 hours, then it was cooled to room temperature and quenched with water (20 ml). The resultant mixture was extracted with ethyl acetate (10 ml), and the organic layer retained. The aqueous was re-extracted with ethyl acetate (3×10 ml), and the organic fractions were combined, washed with water (3×15 ml), and brine (20 ml), dried (Na$_2$SO$_4$), filtered and concentrated in vacuo to give the crude material. This was purified by silica column chromatography (1:98.9:0.1 to 2:97.8:0.2 methanol:dichloromethane:ammonia). The appropriate fractions were concentrated in vacuo to yield the title compound as a 1:1 mixture of diastereoisomers as a colourless oil, (47 mg, 35%).

NMR (C$_6$D$_6$) (Selected data for the free base): (1:1 mixture of diastereomers) 0.75 and 0.8 (2×d, 3H), 1.0 and 1.05 (2×s, 3H), 4.9 and 4.95 (m, 1H), 6.6–7.5 (m, 9H).

MS (API+): M/Z [MH$^+$]340.3; C$_{22}$H$_{29}$NO$_2$+H requires 340.45.

Example 11

(±)-4-(3-Hydroxyphenyl)-N-((S)-3-hydroxy-3-phenylpropyl)-trans-3,4-dimethylpiperidine The procedure of example 10 was followed but using S-(−)-1-chloro-3-hydroxy-3-phenylpropane in place of R-(+)-1-chloro-3-hydroxy-3-phenylpropane to yield 51 mg, 38% of a 1:1 mixture of diastereoisomers.

NMR (C$_6$D$_6$) (Selected data for the free base): (1:1 mixture of diastereoisomers) 0.8 and 0.85 (2×d, 3H), 1.0 and 1.05 (2×s, 3H), 4.9 and 4.95 (m, 1H), 6.6–7.5 (m, 9H).

MS (API+): M/Z [MH$^+$]340.2; C$_{22}$H$_{29}$NO$_2$+H requires 340.45.

Example 12

(±)-N-((S)-3-Cyclohexyl-3-hydroxypropyl)-4-(3-hydroxyphenyl)-trans-3,4-dimethylpiperidine To a stirred solution of (±)-4-(3-hydroxyphenyl)-trans-3,4-dimethylpiperidine (0.2 g, 0.97 mmol) in 1,2-dimethoxyethane (10 ml) was added sodium hydrogen carbonate (0.122 g, 1.455 mmol) and (S)-3-cyclohexyl-3-hydroxypropyl (4-bromobenzenesulfonate) [prepared in direct analogy with Werner et al., J. Org. Chem. 1996, 61, 587] (0.368 g, 0.97 mmol). The stirred reaction mixture was heated under reflux for 16 hours, cooled to room temperature and stirred for 1 hour at 0° C. The resulting white precipitate was removed by filtration through celite and washed with tetrahydrofuran (5 ml). The filtrate was washed with a saturated aqueous solution of potassium carbonate (2×10 ml) and brine (10 ml). The resulting organic phase was dried (MgSO$_4$), filtered and concentrated in vacuo to give the crude material which was purified by silica (10 g) column chromatography, eluting with dichloromethane, followed by dichloromethane ethyl acetate (1:1), to give the title compound as a brown oil, (87 mg, 26%).

NMR (CDCl$_3$) (Selected data for free base): 0.6 (d, 3H), 1.3 (s, 3H), 1.5 (m, 2H), 1.7–1.9 (m, 2H), 1.6–1.75 (m, 5H), 1.9 (m, 2H), 2.85 (m, 1H), 6.5–6.6 (m, 1H), 6.65 (m, 2H), 7.05 (m, 6H).

MS (thermospray): M/Z [MH$^+$]346.3; C$_{22}$H$_{35}$NO$_2$+H requires 346.28.

Example 13

(±)-(3-Acetoxyphenyl)-N-(n-hexyl)-trans-3,4-dimethylpiperidine hydrochloride

A dry round-bottomed flask was charged with (±)-N-(n-hexyl)-4-(3-hydroxyphenyl)-trans-3,4-dimethylpiperidine hydrochloride (114 mg, 0.39 mmol), triethylamine (1 ml) and dichloromethane (5 ml). The stirred reaction mixture was cooled to 0° C. and acetyl chloride (0.055 ml, 0.78 mmol) was added dropwise. After 4 hours the reaction mixture was diluted with water (10 ml) and extracted with dichloromethane (3×25 ml). The organic fractions were dried (Na$_2$SO$_4$), filtered and concentrated in vacuo to give the crude product. This was purified by silica (5 g) column chromatography eluting with ethylacetate:hexane (3:7)+1% ammonia to give the title compound as an oil (79 mg, 56%). The oil was dissolved in dry ether (2 ml) and 1.1 mol equivalents of 1N ethereal hydrogen chloride solution was added to provide a precipitate which was collected by filtration and dried in a vacuum oven to yield the title compound as a white solid. m.p. 165–167° C.

NMR (CDCl$_3$) (Selected data on hydrochloride salt): 0.8 (d, 3H), 2.3 (s, 3H), 3.7 (m, 2H), 6.9–7.4 (m, 4H), 11.5 and 12.3 (2×bs, 1H).

MS (thermospray): M/Z [MH$^+$]332.3; C$_{21}$H$_{33}$NO$_2$+H requires 332.5.

BIOLOGICAL ACTIVITY

The compounds of the invention are evaluated for their activity as antipruritic agents by measuring their ability to inhibit the hind leg scratching behaviour induced in rats by the administration of a known pruritogenic agent. These studies are based on the procedure described by Berendsen and Broekkamp in the European Journal of Pharmacology, 1991, 194, 201. The test is performed as follows:

Male Wistar rats (approximately 150 g body weight) are challenged with a pruritogen by subcutaneous injection of 5-methoxytryptamine hydrochloride (4 mg/3 ml/kg) dissolved in physiological saline into the scruff of the neck. At this dose a constant and quantifiable hindleg scratching response lasting up to 90 minutes is obtained.

The test compound is administered to the test animals by subcutaneous injection in an aqueous micelle formulation. The test compound is prepared in the following manner. The compound is dissolved in vehicle (composition v/v %: glycerol formal, 24; tween 80, 17; benzyl alcohol, 1.5 and purified water to 100) then seven parts purified water is added to three parts vehicle to give the aqueous micelle formulation. The compounds can be administered pre- or post-challenge or may be co-administered with the pruritogenic challenge.

After the pruritogen challenge hindleg scratching is scored for each animal by recording the presence or absence of scratching during each 30 second interval as 1 or 0 scored respectively. The score for each animal is totalled after 25 minutes (maximum score 50). The efficacy of compounds is assessed by their ability to significantly reduce the score in treated groups compared to the control group for which the score is approximately around 30. Antipruritic activity for test compounds is expressed as a percentage reduction of hindleg scratching using the following formula:

$$\frac{(a-b)}{a} \times 100,$$

when
a is the mean hindleg scratching score of untreated and challenged rats.
b is the mean hindleg scratching score of treated and challenged rats.

Using the above test the following results were obtained.

| COMPOUND | DOSE (mg/kg) | % REDUCTION OF SCRATCH |
|---|---|---|
| Example 1 | 10 | 90 |
| Example 2(+)-enantiomer | 10 | 95 |
| Example 2(−)-enantiomer | 10 | 82 |
| Example 3 | 10 | 92 |
| Example 4 | 10 | 75 |
| Example 5 | 10 | 82 |
| Example 6 | 10 | 69 |
| Example 7 | 10 | 54 |
| Example 8 | 10 | 94 |
| Example 9 | 10 | 80 |
| Example 10 | 10 | 77 |
| Example 11 | 10 | 85 |
| Example 12 | 10 | 81 |
| Example 13 | 10 | 90 |

Antipruritic activity was also demonstrated in dogs suffering from flea allergy dermatitis. Administration by subcutaneous injection significantly reduced scratching behaviour at a dose level of 1–10 mg/kg.

We claim:

1. A method for treating pruritus in a human or animal subject, which comprises administering to said subject a therapeutically or prophylactically effective amount of:

(i) a compound of formula I:

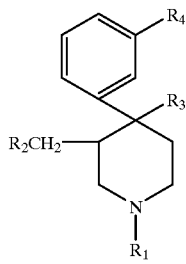

Formula I wherein in formula I above $R_1$ is $C_1$–$C_8$ alkyl, $C_3$–$C_8$ alkenyl, $C_3$–$C_8$ alkynyl, $C_4$–$C_8$ (cycloalkyl)alkyl,

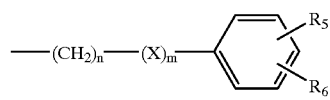

or

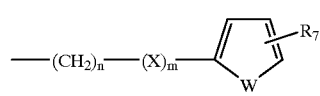

wherein n is 1, 2 or 3;

m is 0 or 1;

X is C(=O), CH(OH), CH=CH, S, O, or $NR_8$, wherein $R_8$ is H, $C_1$–$C_4$ alkyl or $C_1$–$C_4$ alkanoyl;

Z is C(=O), CH(OH), or CH=CH;

W is O or S;

$R_5$ is $C_1$–$C_3$ alkylthio, nitro, amino, trifluoromethyl, hydroxy, or $R^6$;

$R_6$ is H, $C_1$–$C_3$ alkyl, $C_1$–$C_3$ alkoxy, or halogen;

$R_7$ is H or methyl;

$R_2$ is H, $C_1$–$C_4$ alkyl, or $C_2$–$C_6$ alkenyl;

$R_3$ is $C_1$–$C_4$ alkyl or $C_2$–$C_6$ alkenyl; and $R_4$ is H, hydroxy, $C_1$–$C_3$ alkoxy, $C_1$–$C_{12}$ alkanoyloxy, or

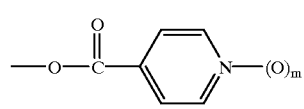

or

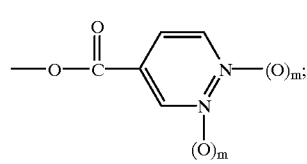

or a pharmaceutically or veterinarily acceptable salt thereof; with the limitation that when X or Z is CH(OH) or C(=O), n is other than 3; or (ii) a compound of the formula 2:

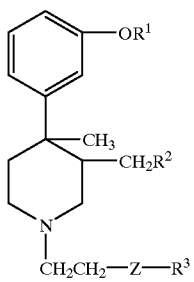

Formula 2 wherein in formula 2 above
$R^1$ is H or $C_1$–$C_4$ alkanoyl;
$R^2$ is H, $C_1$–$C_4$ alkyl or $C_2$–$C_6$ alkenyl;
$R^3$ is $C_4$–$C_8$ cycloalkyl, $C_4$–$C_8$ cycloalkenyl, $C_1$–$C_6$ alkyl, $C_2$–$C_6$ alkenyl, $C_1$–$C_4$ alkyl substituted $C_4$–$C_8$ cycloalkyl, $C_1$–$C_4$ alkyl substituted $C_4$–$C_8$ cycloalkenyl or thienyl;
Z is CH(OR$^4$), C(=O), or a bond;
$R^4$ is hydrogen, $C_1$–$C_6$ alkyl,

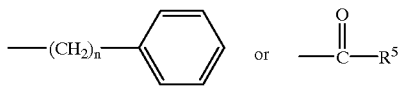

$R^5$ is $C_1$–$C_4$ alkyl or

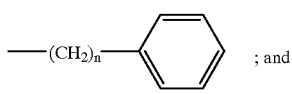
; and n is 1, 2 or 3;
or a pharmaceutically or veterinarily acceptable salt thereof; or
(iii) a compound of the formula 3:

Formula 3

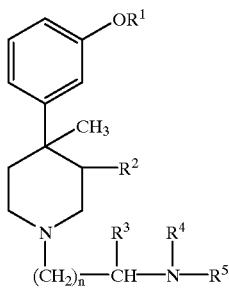

wherein in formula 3 above
$R^1$ is H or ($C_1$–$C_5$) alkyl;
$R^2$ is H, ($C_1$–$C_5$) alkyl, or ($C_2$–$C_6$) alkenyl;
$R^3$ is H, ($C_1$–$C_{10}$) alkyl, ($C_3$–$C_8$) cycloalkyl; ($C_3$–$C_{10}$) alkenyl, ($C_3$–$C_8$) cycloalkyl ($C_1$–$C_3$) alkyl, phenyl, ($C_5$–$C_8$) cycloalkenyl, ($C_5$–$C_8$) cycloalkenyl-($C_1$–$C_3$) alkyl, or phenyl-($C_1$–$C_3$)alkyl;
$R^4$ is H, ($C_3$–$C_8$) cycloalkyl, ($C_1$–$C_{10}$) alkyl, ($C_3$–$C_{10}$) alkenyl, ($C_3$–$C_8$) cycloalkyl-($C_1$–$C_3$)alkyl, phenyl or phenyl-($C_1$–$C_3$) alkyl;

$R^5$ is H, ($C_1$–$C_{10}$)alkyl ($C_1$–$C_{10}$)alkanoyl, C(O)CH—[(CH$_2$)$_3$NHC(NH)NHNO$_2$]—NHC(O)W, C(O)NH($C_1$–$C_{10}$)alkyl, [C(O)—(CH$_2$)$_m$C(O)]$_q$R$^6$, or [C(O)(CH$_2$)$_m$NHC(O)]$_q$-R$^{6-}$,
W is ($C_1$–$C_{10}$)alkyl, O($C_1$–$C_{10}$)alkyl, ($C_1$–$C_4$ alkyl)-NHC(O) ($C_1$–$C_6$)-alkyl, or ($C_1$–$C_4$ alkyl)C(O)NHB, where B is ($C_1$–$C_{10}$)-alkyl, phenyl or phenyl-($C_1$–$C_3$) alkyl;
$R^6$ is OR$^7$; NHR$^7$, OCH$_2$C(O)NR$^8$R$^9$, O($C_1$–$C_4$ alkyl) OC—(O)R$^{10}$, ($C_1$–$C_{10}$) alkyl or NHCHR$^{11}$C(O)R$^{12-}$,
$R^7$ is H, ($C_1$–$C_{10}$)alkyl, ($C_3$–$C_8$)cycloalkyl, ($C_3$–$C_8$) cycloalkyl-($C_1$–$C_3$)alkyl or (CH$_2$)$_m$C(O)NR$^8$R$^{9-}$,
$R^8$ is H, or ($C_1$–$C_{10}$)alkyl;
$R^9$ is H, or ($C_1$–$C_{10}$)alkyl;
$R^{10}$ is ($C_1$–$C_{10}$) alkyl, ($C_3$–$C_8$) cycloalkyl, or

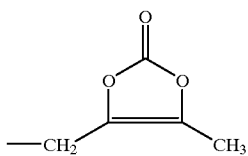

$R^{11}$ is H, ($C_1$–$C_{10}$)alkyl, or phenyl-($C_1$–$C_3$)alkyl;
$R^{12}$ is OR$^{13}$ or NR$^{13}$R$^{14}$;
$R^{13}$ is H or ($C_1$–$C_{10}$)alkyl;
$R^{14}$ is H or ($C_1$–$C_{10}$)alkyl;
n=1–3;
m=1–3;
q=1–3; or a pharmaceutically or veterinarily acceptable salt thereof; or
(iv) a compound of the formula 4:

Formula 4 wherein in formula 4 above;
$R^1$ is H or $C_1$–$C_5$ alkyl;
$R_2$ is H, $C_1$–$C_5$ alkyl or $C_2$–$C_6$ alkenyl;
$R_3$ is H, $C_1$–$C_{10}$ alkyl, $C_1$–$C_{10}$ alkenyl, phenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;
A is OR$^4$ or NR$^5$R$^6$;
wherein:
$R^4$ is H, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;
$R^5$ is H or $C_1$–$C_3$ alkyl;
$R^6$ is H, $C_1$–$C_{10}$ alkyl, $C_3$–$C_{10}$ alkenyl, cycloalkyl, phenyl, cycloalkyl-substituted $C_1$–$C_3$ alkyl, $C_5$–$C_8$ cycloalkenyl, $C_5$–$C_8$ cycloalkenyl-substituted $C_1$–$C_3$ alkyl, phenyl-substituted $C_1$–$C_3$ alkyl, or (CH$_2$)$_q$—B;
or $R^5$ and $R^6$ are each $CH_2$ which together with N form a 4- to 6-membered heterocyclic ring:
wherein:
B is:

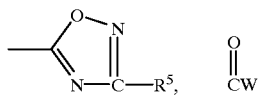

or $NR^7R^8$ wherein:
$R^7$ is H or $C_1$–$C_3$ alkyl;
R is H, $C_1$–$C_{10}$ alkyl, $C_3$–$C_{10}$ alkenyl, cycloalkyl-substituted $C_1$–$C_3$ alkyl, cycloalkyl, $C_5$–$C_8$ cycloalkenyl, $C_5$–$C_8$ cycloalkenyl-substituted $C_1$–$C_3$ alkyl, phenyl or phenyl-substituted $C_1$–$C_3$ alkyl; or
$R^7$ and $R^8$ are each $CH_2$ which together with N form a 4- to 6-membered heterocyclic ring;
W is $OR^9$, $NR^{10}OR^{11}$ or OE;
wherein:
$R^9$ is hydrogen, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;
$R^{10}$ is hydrogen or $C_1$–$C_3$ alkyl;
$R^{11}$ is hydrogen, $C_1$–$C_{10}$ alkyl, $C_3$–$C_{10}$ alkenyl, phenyl, cycloalkyl, $C_5$–$C_8$ cycloalkenyl, cycloalkyl-substituted $C_1$–$C_3$ alkyl, phenyl-substituted $C_1$–$C_3$ alkyl, or

or
$R^{10}$ and $R^{11}$ are each $CH_2$ which together with N form a 4- to 6-membered heterocyclic ring;
E is

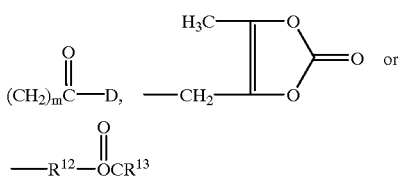

wherein:
$R^{12}$ is $C_1$–$C_3$ alkyl substituted methylene,
$R^{13}$ is $C_1$–$C_{10}$ alkyl;
D is $OR^{14}$ or $NR^{15}R^{16}$;
wherein:
$R^{14}$ is H, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, or $C_5$–$C_8$ cycloalkenyl-substituted $C_1$–$C_3$ alkyl or phenyl-substituted $C_1$–$C_3$ alkyl;
$R^{15}$ is H, $C_1$–$C_{10}$ alkyl, $C_3$–$C_{10}$ alkenyl, phenyl, phenyl-substituted $C_1$–$C_3$ alkyl, cycloalkyl, $C_5$–$C_8$ cycloalkenyl, cycloalkyl-substituted $C_1$–$C_3$ alkyl or $C_5$–$C_8$ cycloalkenyl-substituted $C_1$–$C_3$ alkyl;
$R^{16}$ is H or $C_1$–$C_3$ alkyl;
$R^{15}$ and $R^{16}$ are each $CH_2$ which together with N form a 4- to 6-membered heterocyclic ring;
Y is $OR^{11}$ or $NR^{18}R^{19}$;

wherein:
$R^{17}$ is H, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl, or phenyl-substituted $C_1$–$C_3$ alkyl;
$R^{18}$ is hydrogen or $C_1$–$C_3$ alkyl;
$R^{19}$ is hydrogen, $C_1$–$C_{10}$ alkyl, $C_3$–$C_{10}$ alkenyl, phenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl, or phenyl-substituted $C_1$–$C_3$ alkyl; or
$R^{18}$ and $R^{19}$ are each $CH_2$ which together with N form a 4- to 6-membered heterocyclic ring;
n is 0–4;
q is 1–4;
m is 1–4;
or a pharmaceutically or veterinarily acceptable salt thereof.

2. A method as claimed in claim 1 wherein said compound administered is a compound of the formula:

Formula 5

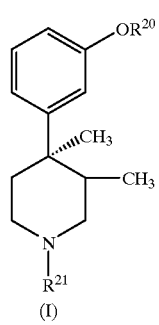

(I)

or a pharmaceutically or veterinarily acceptable salt thereof wherein in Formula 5 above:
$R^{20}$ is H or $C_1$–$C_4$ alkanoyl;
$R^{21}$ is $C_1$–$C_8$ alkyl, $C_3$–$C_8$ alkenyl, $C_3$–$C_8$ alkynyl, $C_3$–$C_8$ cycloalkyl($C_1$–$C_6$)alkyl, $C_5$–$C_8$ cycloalkenyl($C_1$–$C_6$) cycloalkyl, or a group of the formula —$(CH_2)_n$—G—Ar;
wherein n is 1, 2 or 3;
G is C=O, CH(OH), O or a direct bond; and
$A_1$ is $C_3$–$C_8$ cycloalkyl, phenyl, which may optionally be substituted with one or more substituents independently selected from halo, $C_1$–$C_4$ alkyl, ($C_1$–$C_4$) alkoxy, or $A_1$ is thienyl, furyl, or pyridyl.

3. A method as claimed in claim 2 wherein said compound administered is of the formula 5 wherein $R^{20}$ is H or $COCH_3$ and $R^{21}$ is $C_2$–$C_8$ alkyl or $C_1$–$C_8$ alkyl substituted by $C_3$–$C_8$ cycloalkyl.

4. A method as claimed in claim 3 wherein said compound administered is of the formula 5 wherein $R^{21}$ is n-hexyl, 2-methylpentyl or cyclohexylethyl.

5. A method as claimed in claim 2 wherein said compound administered is of the formula 5 wherein said compound is:
(±)-N-(n-hexyl)-4-(3-hydroxyphenyl)-trans-3,4-dimethylpiperidine hydrochloride;
(±)-4-(3-hydroxyphenyl)-trans-3,4-dimethyl-N-(4-methylpentyl)piperidine hydrochloride;
(±)-4-(3-hydroxyphenyl)-trans-3,4-dimethyl-N-[(3-(thien-3-yl)prop-1-yl]piperidine;
(±)-N-(2-cyclohexylethyl)-4-(3-hydroxyphenyl)-trans-3,4-dimethylpiperidine hydrochloride;

(±)-4-(3-hydroxyphenyl)-trans-3,4-dimethyl-N-[(3-(thien-2-yl)prop-1-yl]piperidine;

(±)-4-(3-hydroxyphenyl)-trans-3,4-dimethyl-N-(3-phenylpropyl)piperidine;

(±)-4-(3-hydroxyphenyl)-trans-3,4-dimethyl-N-(2-phenoxyethyl)piperidine;

(±)-N-(3-cyclohexylpropyl)-4-(3-hydroxyphenyl)-trans-3,4-dimethylpiperidine;

(±)-N-(3-hydroxyphenyl)-N-((R)-3-hydroxy-3-phenylpropyl)-trans-3,4-dimethylpiperidine;

(±)-N-(3-hydroxyphenyl)-N-((S)-3-hydroxy-3-phenylpropyl)-trans-3,4-dimethylpiperidine;

(±)-N-((S)-3-cyclohexyl-3-hydroxypropyl)-4-(3-hydroxyphenyl)-trans-3,4-dimethylpiperidine; and (±)-(3-acetoxyphenyl)-N-(n-hexyl)-trans-3,4-dimethylpiperidine hydrochloride.

6. A method for treating pruritus in animals as claimed in claim 1, wherein said compound is administered to an animal subject that is selected from cats, dogs and horses.

* * * * *